United States Patent
Keil (10) Patent No.: US 11,243,285 B2
(45) Date of Patent: Feb. 8, 2022

(54) METHOD FOR PERFORMING AN ANGIOGRAPHIC MEASUREMENT

(71) Applicant: Siemens Healthcare GmbH, Erlangen (DE)

(72) Inventor: Miriam Keil, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 820 days.

(21) Appl. No.: 15/992,294

(22) Filed: May 30, 2018

(65) Prior Publication Data
US 2018/0356485 A1    Dec. 13, 2018

(30) Foreign Application Priority Data
Jun. 7, 2017    (EP) .................................... 17174697

(51) Int. Cl.
*G01R 33/563* (2006.01)
*A61B 5/026* (2006.01)
(Continued)

(52) U.S. Cl.
CPC ...... *G01R 33/56316* (2013.01); *A61B 5/0263* (2013.01); *G01R 33/281* (2013.01);
(Continued)

(58) Field of Classification Search
CPC .......... G01R 33/56316; G01R 33/5601; G01R 33/56308; G01R 33/5635; G01R 33/56;
(Continued)

(56) References Cited

U.S. PATENT DOCUMENTS 5,928,148 A    7/1999 Wang et al.
6,215,305 B1 *  4/2001 Haselhoff ............ G01R 33/543
                                                    324/300
(Continued)

FOREIGN PATENT DOCUMENTS

CN    103126673 A    6/2013
CN    106073811 A    11/2016
(Continued)

OTHER PUBLICATIONS

Localizer (SCOUT) images—OTpedia, information for medical imaging, (n.d.). Retrieved Feb. 27, 2021, from http://www.otpedia.com/entryDetails.cfm?id=398 (Year: 2021).*
(Continued)

*Primary Examiner* — Amelie R Davis
*Assistant Examiner* — Helene Bor
(74) *Attorney, Agent, or Firm* — Harness, Dickey & Pierce, P.L.C.

(57) ABSTRACT

A method is for performing an angiographic measurement of a main measurement region of a patient via a magnetic resonance system. An embodiment of the method includes performing at least one overview measurement to generate overview-measurement data; defining, using the overview-measurement data, the main measurement region and a first measurement region, the first measurement region differing from the main measurement region; performing a first time-resolved measurement in the first measurement region defined to generate first time-resolved measurement data; detecting an injected contrast agent bolus in the first measurement region using the first time-resolved measurement data; determining a flow rate of the injected contrast agent bolus detected; setting at least one measurement parameter of the angiographic measurement according to the flow rate determined; and performing the angiographic measurement
(Continued)

of the main measurement region of the patient in the magnetic resonance system using the at least one measurement parameter set.

26 Claims, 2 Drawing Sheets

(51) Int. Cl.
    *G01R 33/56* (2006.01)
    *G01R 33/28* (2006.01)
    *G01R 33/54* (2006.01)
    *A61B 5/055* (2006.01)

(52) U.S. Cl.
    CPC ........... *G01R 33/543* (2013.01); *G01R 33/56* (2013.01); *G01R 33/5601* (2013.01); *G01R 33/563* (2013.01); *G01R 33/5635* (2013.01); *G01R 33/56308* (2013.01); *A61B 5/055* (2013.01)

(58) Field of Classification Search
    CPC .. G01R 33/563; G01R 33/281; G01R 33/543; A61B 5/0263; A61B 5/055
    See application file for complete search history.

(56) References Cited

U.S. PATENT DOCUMENTS

| | | | | |
|---|---|---|---|---|
| 8,208,699 | B2* | 6/2012 | Hay | A61B 6/488 |
| | | | | 382/128 |
| 10,620,285 | B2* | 4/2020 | Grodzki | G01R 33/543 |
| 2001/0019265 | A1* | 9/2001 | Matsushima | G01R 33/54 |
| | | | | 324/307 |
| 2002/0091316 | A1* | 7/2002 | Foo | G01R 33/563 |
| | | | | 600/420 |
| 2006/0178836 | A1* | 8/2006 | Bai | G16H 50/50 |
| | | | | 702/19 |
| 2008/0180104 | A1* | 7/2008 | Furudate | G01R 33/56375 |
| | | | | 324/318 |
| 2012/0271158 | A1 | 10/2012 | Schmitt | |
| 2013/0137967 | A1 | 5/2013 | Lui et al. | |
| 2015/0097562 | A1 | 4/2015 | Grodzki et al. | |
| 2016/0317113 | A1 | 11/2016 | Allmendinger et al. | |
| 2016/0325040 | A1 | 11/2016 | Flohr et al. | |
| 2018/0284210 | A1* | 10/2018 | Keil | G01R 33/4818 |

FOREIGN PATENT DOCUMENTS

| | | |
|---|---|---|
| CN | 106108928 A | 11/2016 |
| DE | 102011007835 A1 | 10/2012 |
| DE | 102013220288 A1 | 4/2015 |
| EP | 3093678 A1 | 11/2016 |
| WO | WO 2016180799 A1 | 11/2016 |

OTHER PUBLICATIONS

Extended European Search Report #17174697.7 dated Dec. 19, 2017.
Chinese Office Action and English translation thereof dated May 22, 2020.
Chinese Notice of Allowance and English translation thereof dated Dec. 24, 2020.

* cited by examiner

METHOD FOR PERFORMING AN ANGIOGRAPHIC MEASUREMENT

PRIORITY STATEMENT

The present application hereby claims priority under 35 U.S.C. § 119 to European patent application number EP 17174697.7 filed Jun. 7, 2017, the entire contents of which are hereby incorporated herein by reference.

FIELD

At least one embodiment of the invention generally relates to a method for performing an angiographic measurement of a main measurement region of a patient by way of a magnetic resonance system, to the associated magnetic resonance system and to an associated computer program product.

BACKGROUND

In a magnetic resonance system, a main magnet is normally used to apply a relatively high main magnetic field, for example of 1.5 or 3 or 7 tesla, to a body to be examined of a person under examination, in particular of a patient. In addition, a gradient coil unit is used to output gradient pulses. High frequency RF pulses, in particular excitation pulses, are then emitted via a radio frequency antenna unit using suitable antenna devices, causing the nuclear spins of certain atoms, which have been excited to resonance by these radio frequency pulses, to be tipped by a defined flip angle with respect to the magnetic field lines of the main magnetic field. Radio frequency signals, known as magnetic resonance signals, are emitted when the nuclear spins relax, which signals are received by suitable radio frequency antennas and then processed further. Finally, the desired images can be reconstructed from the measurement data acquired in this manner.

An angiographic measurement in a magnetic resonance system is a known examination method for depicting the arterial and/or venous vascular system. Particular thought is needed for setting the measurement parameters, in particular the time sequence, of the angiographic measurement. One reason for this is that for the angiographic measurement, a contrast agent is injected that strengthens the signal from the blood vessels compared with the signal from the surrounding tissue, and that the dispersion of the contrast agent in the body is meant to be detected. Contrast agents containing gadolinium are usually injected. By acquiring measurement data before and after the injection of the contrast agent, the surrounding tissue can be practically eliminated by subtracting the images reconstructed from the measurement data. Therefore in the angiographic measurement it is necessary to start the angiographic measurement at an optimum time after the injection of the contrast agent bolus in order to achieve an optimum image contrast.

Various methods have been used to date in order to set optimally the measurement parameters of the angiographic measurement. In a first method, a patient is injected initially with a pre-contrast bolus, which comprises a small amount (for instance 1 mL) of contrast agent. A time-resolved measurement simultaneously represents a vessel close to the main measurement region to be examined. By analyzing the signal variation, in particular the contrast within a vascular structure over time, it is possible to determine characteristics of the pre-contrast bolus. Conclusions about characteristics of a main contrast agent bolus, which comprises a standard amount (for instance 8 mL) of contrast agent, can be drawn therefrom, and the measurement parameters of the angiographic measurement can be set accordingly.

In this first method, the patient must usually be injected twice with contrast agent. Moreover, the conclusions must be drawn appropriately; for instance a user must interpret the various characteristics, in particular the different enhancement between the 1 mL contrast agent bolus and the 8 mL contrast agent bolus, so that the measurement parameters, in particular the measurement start time, of the angiographic measurement can be set appropriately.

In a second method, a measurement region close to the main measurement region to be examined is measured continuously by a time-resolved measurement. In particular, a vessel through which an injected contrast agent bolus first flows is observed by the time-resolved measurement while the contrast agent bolus is being injected. As soon as the contrast agent bolus is detected in the vessel, the time-resolved measurement is stopped and the angiographic measurement is started.

This second method is substantially easier to perform than the first method but requires that the measurement parameters of the angiographic measurement are already set correctly in advance, so that the angiographic measurement can be started practically immediately. It is important here, for example, that as a result of medical conditions or other diagnoses, an assumed circulation time of the patient does not differ sharply from the "standard" circulation times assumed for the parameterization of the subsequent angiographic measurement. The circulation time can be used, for example, to infer a flow rate of the contrast agent bolus or the blood flow rate.

DE 10 2013 220 288 B4 discloses a method for acquiring magnetic resonance image data, an image-data acquisition unit, a magnetic resonance system and a computer program product, in which control commands for a magnetic resonance system are optimized and tested.

DE 10 2011 007 835 A1 describes a method for producing a magnetic resonance angiogram of a vascular structure of a region under examination, in which method, spins in the region under examination are saturated by applying at least one RF saturation pulse, and in the subsequent magnetic resonance signal acquisition for producing the magnetic resonance angiogram, have a lower signal intensity than spins that flow into the region under examination from a main artery via a supply artery and that are not saturated by the at least one RF saturation pulse and have a far higher signal intensity than the saturated spins.

SUMMARY

At least one embodiment of the invention defines a method for performing a versatile and/or fast angiographic measurement of a main measurement region of a patient via a magnetic resonance system, and to define the magnetic resonance system and the computer program product.

The claims define advantageous developments.

Embodiments of the invention are described below both with reference to the magnetic resonance system and with reference to the method. Features, advantages or alternative embodiments mentioned in this connection can also be applied equally to the other claimed subject matter, and vice versa. In other words, the existing claims (which claims are directed at a magnetic resonance system, for example) can also be developed by combining with features described or claimed in connection with a method. The corresponding functional features of the method are embodied in this case by corresponding physical modules.

The method according to at least one embodiment of the invention is for performing an angiographic measurement of a main measurement region of a patient via a magnetic resonance system, the method comprising:

performing at least one overview measurement via the magnetic resonance system, wherein overview-measurement data is generated;

using the overview-measurement data to define the main measurement region and a first measurement region, which differs from the main measurement region;

performing a first time-resolved measurement in the defined first measurement region via the magnetic resonance system, wherein first time-resolved measurement data is generated;

using the first time-resolved measurement data to detect an injected contrast agent bolus in the defined first measurement region;

determining a flow rate of the detected injected contrast agent bolus;

setting at least one measurement parameter of the angiographic measurement according to the determined flow rate; and performing the angiographic measurement of the main measurement region of the patient in the magnetic resonance system using the at least one measurement parameter that has been set.

At least one embodiment of the invention relates not only to the method but also to a magnetic resonance system comprising a planning unit, a control unit and a measurement unit, which is designed to perform at least one embodiment of the method according to at least one embodiment of the invention. The statements made above relating to the method according to at least one embodiment of the invention can be applied analogously to the magnetic resonance system. Thus the magnetic resonance system is designed to implement a method for performing an angiographic measurement of a main measurement region of a patient.

The magnetic resonance system can comprise additional components, in particular a contrast-agent injector, that are needed and/or advantageous for performing a method according to at least one embodiment of the invention. Computer programs and further software, by which a processor of the planning unit and/or of the control unit and/or of the measurement unit automatically controls and/or performs a method sequence of a method according to at least one embodiment of the invention, can be stored on a memory unit of the planning unit and/or of the control unit and/or of the measurement unit.

Most of the components of the magnetic resonance system according to at least one embodiment of the invention can be embodied in the form of software components. In principle, however, some of these components can also be implemented in the form of software-aided hardware components, for instance FPGAs or the like, in particular when especially fast calculations are needed. Likewise, the required interfaces can be designed as software interfaces, for instance if all that is involved is a transfer of data from other software components. They can also be designed, however, as hardware-built interfaces driven by suitable software. Of course it is also conceivable that a plurality of the specified components are combined in the form of a single software component or software-aided hardware component.

The computer program product according to at least one embodiment of the invention can be loaded directly into a memory of a programmable control unit of a magnetic resonance system, and comprises program code segments in order to perform a method according to at least one embodiment of the invention when the computer program product is executed in the control unit of the magnetic resonance system. The computer program product may be a computer program or comprise a computer program. The method according to at least one embodiment of the invention can thereby be performed quickly, reproducibly and robustly.

The computer program product is configured such that it can use the control unit to perform the method steps according to at least one embodiment of the invention. Therefore, the control unit must have the necessary specification such as, for example, a suitable RAM, a suitable graphics card or a suitable logic unit, in order to be able to perform the respective method steps efficiently. The computer program product is stored, for example, on a computer-readable medium or on a network or server, from where it can be loaded into the processor of a local processing unit, which may be connected directly to the magnetic resonance system or may form part of the magnetic resonance system.

In addition, control data of the computer program product can be stored on an electronically readable data storage medium. The control data in the electronically readable data storage medium can be embodied such that it performs a method according to at least one embodiment of the invention when the data storage medium is used in a control unit of the magnetic resonance system. Thus the computer program product can also constitute the electronically readable data storage medium. Examples of electronically readable data storage media are a DVD, a magnetic tape, a hard disk or a USB stick, on which is stored electronically readable control data, in particular software (see above). When this control data (software) is read from the data storage medium and stored in the control unit and/or in the planning unit and/or in the measurement unit of the magnetic resonance system, all the embodiments according to at least one embodiment of the invention of the above-described method can be performed. Hence at least one embodiment of the invention can also proceed from the computer-readable medium and/or from the electronically readable data storage medium.

BRIEF DESCRIPTION OF THE DRAWINGS

Further advantages and details of the present invention are presented in the example embodiments described below and with reference to the drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules.

Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention is for performing an angiographic measurement of a main measurement region of a patient via a magnetic resonance system, the method comprising:

performing at least one overview measurement via the magnetic resonance system, wherein overview-measurement data is generated;

using the overview-measurement data to define the main measurement region and a first measurement region, which differs from the main measurement region;

performing a first time-resolved measurement in the defined first measurement region via the magnetic resonance system, wherein first time-resolved measurement data is generated;

using the first time-resolved measurement data to detect an injected contrast agent bolus in the defined first measurement region;

determining a flow rate of the detected injected contrast agent bolus;

setting at least one measurement parameter of the angiographic measurement according to the determined flow rate; and performing the angiographic measurement of the main measurement region of the patient in the magnetic resonance system using the at least one measurement parameter that has been set.

The method according to at least one embodiment of the invention can thus allow the angiographic measurement to be performed in a versatile and faster manner. Therefore at least one embodiment of the invention offers, in particular, a number of advantages:

1) The at least one measurement parameter of the angiographic measurement can be set according to the determined flow rate such that the angiographic measurement is performed during high contrast-enhancement by the injected contrast agent bolus. In the proposed procedure, only a single injection of the contrast agent bolus is typically needed for setting the at least one measurement parameter according to the flow rate of the contrast agent bolus, which flow rate is determined on a patient-specific basis, and for performing the angiographic measurement. Thus advantageously the angiographic measurement can be parameterized optimally and also be started promptly.

2) The at least one measurement parameter of the angiographic measurement is set on the basis of a specific patient, in particular in relation to the circulation and/or the flow rate of the injected contrast agent bolus. The measurement data acquired while the angiographic measurement is being performed can be used to reconstruct or produce angiographic images. A reliable diagnosis for different patients is preferably ensured by way of the angiographic images.

3) By virtue of the standardization of the angiographic measurement, the preparation and implementation of the angiographic measurement can also be automated, for instance by landmark detection.

The main measurement region typically comprises a body region of the patient and in particular a volume. The main measurement region is preferably a subregion of a maximum field of view of the magnetic resonance system. The angiographic measurement is usually performed in the main measurement region of the patient, so that measurement data can be acquired during the angiographic measurement, with the angiographic images reconstructed from the measurement data depicting the main measurement region.

The patient may have a diagnosis or a medical condition, for example; alternatively, the patient may also be a healthy person under examination. In principle, it is also conceivable that the patient may be another subject, in particular may be an animal.

The at least one overview measurement can comprise an overview measurement region in which the overview measurement is performed. In particular, the overview measurement region does not correspond to the main measurement region of the patient. The overview measurement region is normally larger than the main measurement region. At least some, or in particular all, of the main measurement region can typically be contained in the overview measurement region. The overview measurement can preferably have a shorter measurement duration than the angiographic measurement.

Patient-specific parameters such as the body size and body weight are usually captured before the overview measurement, for instance captured by a user of the magnetic resonance system. The magnetic resonance system can comprise suitable device(s) for this. The user can interact in particular with a monitor on which a graphical user interface can be displayed. For instance, the user can define the overview measurement or specifically the overview measurement region of the overview measurement. Alternatively or additionally, it is also conceivable that the at least one overview measurement is performed automatically without the user defining the overview measurement region. The at least one overview measurement may normally be referred to as a localizer. The at least one overview measurement can be used to generate a range of overview-measurement data depending on the configuration of the at least one overview measurement. At least one overview image can be reconstructed or produced from the range of overview-measurement data. A first configuration of the at least one overview measurement may be suitable, for example, for detecting a morphology of the patient. A second configuration of the at least one overview measurement is preferably set for detecting a vascular structure of the patient (vessel localizer).

In principle, it is also conceivable that more than at least one overview measurement, for instance two overview measurements, are performed. The first of the two overview measurements can be configured, for example, preferably to detect the morphology of the patient in the main measurement region. The second of the two overview measurements can be configured, for example, preferably to detect the vascular structure of the patient.

The main measurement region and the first measurement region can be defined in particular by the user. For example, the user can define the main measurement region on the monitor by drag'n'drop by using an input device, in particular a mouse, to interact with the graphical user interface on the monitor. The at least one overview image is preferably used to help define the main measurement region and the first measurement region. For instance, the at least one overview image can be displayed in the background, and the user can define the main measurement region and/or the first measurement region on the at least one overview image. In principle, it is also conceivable that the main measurement region and/or the first measurement region are defined semi-automatically or automatically.

For example, for the semi-automatic definition, the user can select from a list on the graphical user interface a body region, for instance abdomen or chest or thigh. The main measurement region in particular is then defined accordingly on the basis of the selection. The semi-automatic or automatic definition is performed, for example, by landmark detection, which in particular is assisted by sensors and facilitated by a camera, for instance. For the automatic definition of the main measurement region, it is conceivable in particular that the main measurement region is defined without interaction by the user with the graphical user interface, for instance on the basis of information contained in an electronic health record of the patient. The first measurement region can also be defined semi-automatically or automatically in a similar way to the semi-automatic and automatic definition of the main measurement region.

According to at least one embodiment of the invention, the first measurement region differs from the main measurement region. The first measurement region can be defined suitably according to the main measurement region. Alternatively, the main measurement region can be defined according to the first measurement region. The main measurement region and the first measurement region preferably each comprise part of a vascular structure of the patient. The main measurement region can differ from the first measurement region at least in terms of one of the follow parameters:
  a dimension of the volume concerned,
  an orientation of the volume concerned; and
  a position of the volume concerned relative to a coordinate system of the patient.

The main measurement region and the first measurement region preferably, in at least one embodiment, differ in the sense that the volume covered by the first measurement region is not contained in the main measurement region, and vice versa. For example, the volume of the main measurement region comprises the abdomen body region, whereas the first measurement region, in particular the volume of the first measurement region, comprises the lower-arm body region. If the main measurement region comprises the thorax body region, for example, the first measurement region may comprise the upper-arm body region. In this case, the maximum field of view normally comprises the thorax body region and the upper-arm body region.

The maximum field of view of the magnetic resonance system usually comprises the main measurement region and the first measurement region. If the maximum field of view does not comprise the main measurement region and the first measurement region, the first measurement region can be changed, for instance, such that the maximum field of view comprises the first measurement region in addition to the main measurement region. Preferably in this case only the first measurement region can be changed while in particular the main measurement region is kept the same. For instance, a patient couch on which the patient is supported can be moved such that the maximum field of view comprises the main measurement region, or the patient is repositioned.

An injection region for injecting the contrast agent bolus can preferably be selected on the basis of the defined first measurement region. The injection region can be selected such that the injection region lies outside the maximum field of view of the magnetic resonance system. In this case, the maximum field of view can comprise the main measurement region and the first measurement region. For example, the contrast agent bolus can be injected into the lower arm of the patient, and the first measurement region can comprise the upper-arm body region. The time at which the contrast agent bolus is injected is preferably synchronized with a measurement start time of the first time-resolved measurement in order that the injected contrast agent bolus can be detected in the first measurement region. The measurement start time of the first time-resolved measurement preferably lies earlier in time than the injection of the contrast agent bolus.

The first time-resolved measurement is performed in the defined first measurement region by the magnetic resonance system. Thus the first time-resolved measurement data acquired in the first time-resolved measurement in particular represents the first measurement region. The first time-resolved measurement is preferably configured such that a series of measurement data, in particular first time-resolved measurement data, can be generated over time in the defined first measurement region. Usually at least one first portion of the first time-resolved measurement data has been acquired at an earlier point in time than a second portion of the first time-resolved measurement data. It is preferably possible to acquire in the defined first measurement region a first image by way of the first portion of the first time-resolved measurement data, and a second image by way of the second portion of the first time-resolved measurement data, with the first image depicting the first measurement region at an earlier point in time than the second image. In addition, a plurality of images can be acquired if the first time-resolved measurement is configured accordingly.

The first time-resolved measurement data is used to detect the injected contrast agent bolus in the defined first measurement region. The first time-resolved measurement in particular is configured such that the injected contrast agent bolus can be detected in the first time-resolved measurement data. Usually a time resolution of the first time-resolved measurement is suitably defined for detecting the injected contrast agent bolus. Detecting the injected contrast agent bolus can mean simply detecting a different contrast enhancement in the first time-resolved measurement data as a result of the injected contrast agent bolus. The different contrast enhancement can be defined by a threshold value. The first time-resolved measurement is preferably suitably configured for detecting a contrast-enhancement time instant at which the contrast enhancement by the injected contrast agent bolus differs, in particular in relation to another time instant before the contrast enhancement by the injected contrast agent bolus, by more than the threshold value.

The flow rate of the detected injected contrast agent bolus is determined. The flow rate can be a measure of a blood flow rate and/or of a circulation time. A general health condition of the patient can advantageously be inferred from the flow rate. The flow rate in particular affects a contrast-enhancement time period and the start and end of a contrast enhancement in a specific measurement region. The detected contrast agent bolus is used in determining the flow rate.

In another embodiment of the invention, determining the flow rate of the injected contrast agent bolus comprises defining a first path in the first measurement region, determining a first transit time, on the first path, of the injected contrast agent bolus detected in the first measurement region, and using the first path and the first transit time to calculate the flow rate. For example, the first path can be defined such that a first point and a second point are defined in the first measurement region. It is conceivable in particular that the user defines the first point and/or the second point on the graphical user interface, in particular via the input device. The user preferably takes into account the overview-measurement data in defining the first point and/or the second point on the graphical user interface. Alternatively or additionally, it is also conceivable that the first point and the second point, or the first path, are defined automatically. The vascular structure of the patient, for instance, comprises the first path.

According to another embodiment, the first path is defined along the vascular structure of the patient, which structure is detected by way of the overview-measurement data. The first path can then be defined, for example, by the distance, in particular along the vascular structure, between the first point and the second point. The first point and the second point in particular can correspond to a first end and a second end respectively of the first path.

The first transit time, on the first path, of the injected contrast agent bolus detected in the first measurement region is determined, for example, such that in particular the first time-resolved measurement data is used to detect a first contrast-enhancement time instant and a second contrast-enhancement time instant. For example, the first contrast-enhancement time instant is detected at the first point in the first measurement region, and the second contrast-enhancement time instant is detected at the second point in the first measurement region. Alternatively or additionally, the first contrast-enhancement time instant can be detected at the first end of the first path, and the second contrast-enhancement time instant can be detected at the second end of the first path. The first transit time then equals in particular the magnitude of the difference between the first contrast-enhancement time instant and the second contrast-enhancement time instant. The first transit time can also be determined in such a way that the user defines the first path on the graphical user interface for instance by marking a portion of the vascular structure, or the first path is defined automatically, and the first time-resolved measurement data is used to determine the first transit time on the basis of the first end and the second end of the first path. For instance, the magnetic resonance system can comprise at least one component that can determine the first transit time on the basis of the first path.

The flow rate is normally calculated using the first path and the first transit time. For example this is done by dividing the first path by the first transit time.

The at least one measurement parameter of the angiographic measurement is set according to the determined flow rate. The angiographic measurement can comprise a plurality of measurement parameters, which can be categorized differently. For instance, the measurement start time and the measurement end time can be assigned to a first category comprising time parameters. A matrix size, a spatial resolution, a slice thickness and a repetition time are assigned in particular to a second category comprising sequence parameters. For example, changing the at least one sequence parameter causes an adjustment to at least one time parameter, and vice versa. The at least one measurement parameter set according to the determined flow rate is selected in particular either from the first category comprising the time parameters or from the second category comprising the sequence parameters. The at least one measurement parameter can thus be selected from the following list: a measurement start time, a measurement end time, a matrix size, a spatial resolution, a slice thickness, a repetition time of the angiographic measurement. Any combination of the listed measurement parameters can also be set. Of course additional measurement parameters considered practical by a person skilled in the art can also be set.

It is conceivable that the at least one measurement parameter of the angiographic measurement is set by the user. The at least one measurement parameter is preferably set automatically according to the determined flow rate. This is because usually a delay between detecting the injected contrast agent bolus in the first measurement region and the expected contrast enhancement in the main measurement region is not enough to allow the at least one measurement parameter to be set manually, in particular by the user.

Setting the at least one measurement parameter can result in an automatic change to another measurement parameter. By setting the measurement start time of the angiographic measurement, a measurement end time of the first time-resolved measurement can be set, for instance such that the angiographic measurement is started after a pause or immediately after the first time-resolved measurement. This can have the consequence, for example, that the first time-resolved measurement is stopped after the injected contrast agent bolus is detected, and the angiographic measurement is started. In other words, by setting the at least one measurement parameter of the angiographic measurement, another at least one measurement parameter of another measurement, for instance of the time-resolved measurement, can be set, and vice versa.

The at least one measurement parameter can be, for example, a measurement start time or a measurement end time of the angiographic measurement. The measurement start time of the angiographic measurement and the measurement end time of the angiographic measurement can set in particular a measurement duration of the angiographic measurement. The measurement start time and the measurement end time of the angiographic measurement can be set simultaneously according to the determined flow rate, for example. The at least one measurement parameter of the angiographic measurement is preferably set such that the angiographic measurement is performed in a time period containing, in particular optimum, contrast enhancement by the injected contrast agent bolus in the main measurement region. The at least one measurement parameter of the angiographic measurement is normally set such that particularly suitable angiographic images can be obtained while the angiographic measurement is being performed.

The at least one measurement parameter can be set such that the angiographic measurement is performed within the measurement duration. The sequence parameters and the time parameters are usually accountable for a contrast, a signal strength and the measurement duration of the angiographic measurement. Advantageously, the at least one measurement parameter for performing the angiographic measurement is adjusted in terms of the contrast, the signal strength and/or the measurement duration of the angiographic measurement.

For example, the measurement duration of the angiographic measurement can be prolonged by increasing the time interval between the measurement start time of the angiographic measurement and the measurement end time of the angiographic measurement. By setting the at least one measurement parameter, it is possible to set in particular the measurement duration of the angiographic measurement according to the determined flow rate. For instance, the slower the flow rate, the longer is the measurement duration of the angiographic measurement. Typically, the greater the first transit time, the longer is the measurement duration of the angiographic measurement.

Preferably, setting the at least one measurement parameter of the angiographic measurement can involve simply setting the time parameters, in particular for instance shifting the measurement start time of the angiographic measurement and the measurement end time of the angiographic measurement to the same degree. If the measurement start time of the angiographic measurement and the measurement end time of the angiographic measurement are shifted to the same degree, usually no further sequence parameters need to be adjusted, because the measurement duration of the angiographic measurement can thereby remain unchanged.

For example, the at least one measurement parameter of the angiographic measurement can be set already before performing the first time-resolved measurement. Before the flow rate of the injected contrast agent bolus is determined, the at least one measurement parameter in particular may be set according to the default values for the angiographic measurement or on the basis of comparable angiographic measurements for other patients. After the flow rate is determined, the at least one measurement parameter can be redefined according to the flow rate or adjusted according to the determined flow rate.

This is advantageous particularly if the circulation times of the patients differ, for instance, or in particular if there are medical conditions present or other anatomic sizes vary amongst the patients. The angiographic measurement can be performed in particular in a patient-specific manner.

The angiographic measurement of the main measurement region of the patient is performed in the magnetic resonance system using the at least one measurement parameter that has been set. Angiographic measurement data is generated while the angiographic measurement is being performed. Angiographic images, which are used in particular to produce an angiogram, can be reconstructed from the angiographic measurement data.

In another embodiment, the overview-measurement data is used to define a second measurement region, which differs from the first measurement region and from the main measurement region. The second measurement region preferably differs from the main measurement region in the sense that, like the first measurement region, the main measurement region does not comprise the second measurement region, and vice versa.

In one embodiment, the first measurement region is located distal to the main measurement region, and the second measurement region is located proximal to the main measurement region. The first measurement region and the second measurement region are preferably defined such that the injected contrast agent bolus can be detected first in the first measurement region and subsequently in the second measurement region. Thus the distance between the second measurement region and the main measurement region is usually less than the distance between the first measurement region and the main measurement region.

In principle, according to another embodiment, it is conceivable that only the first measurement region or only the second measurement region are defined automatically according to the main measurement region. Alternatively or additionally, it is also conceivable that the first measurement region and the second measurement region are defined, in particular automatically, according to the main measurement region. For example, specifying the body region to be examined can define the main measurement region, and the first measurement region and/or the second measurement region can be defined accordingly. If the first measurement region and/or the second measurement region are defined, usually the corresponding first time-resolved measurement and the second time-resolved measurement are automatically assigned and preferably configured.

According to another embodiment, the maximum field of view of the magnetic resonance system comprises the first measurement region, the second measurement region and the main measurement region. In this case, the magnetic resonance system can perform a measurement in the relevant measurement region without repositioning the patient or without table incrementation of the patient couch. The patient can preferably be positioned in the magnetic resonance system such that the main measurement region of the angiographic measurement is contained in the maximum field of view. The first measurement region and/or the second measurement region can be defined in particular according to the main measurement region, preferably such that the first measurement region and/or the second measurement region likewise lie in the maximum field of view of the magnetic resonance system.

According to one embodiment, setting the at least one measurement parameter of the angiographic measurement comprises performing via the magnetic resonance system a second time-resolved measurement in the defined second measurement region, wherein second time-resolved measurement data is generated, using the second time-resolved measurement data to detect the injected contrast agent bolus in the second measurement region, and setting the measurement start time of the angiographic measurement according to the injected contrast agent bolus detected in the second measurement region.

The second time-resolved measurement is preferably configured such that a second series of measurement data, in particular second time-resolved measurement data, can be generated over time in the defined second measurement region. Usually at least one first portion of the second time-resolved measurement data has been acquired at an earlier point in time than a second portion of the second time-resolved measurement data. It is preferably possible to acquire in the defined second measurement region a first image by way of the first portion of the second time-resolved measurement data, and a second image by way of the second portion of the second time-resolved measurement data, with the first image depicting the second measurement region at an earlier point in time than the second image. In addition, a plurality of images can be acquired if the first time-resolved measurement is configured accordingly.

Furthermore, the second time-resolved measurement data can be used to detect the injected contrast agent bolus in particular in the defined second measurement region. The second time-resolved measurement can preferably be configured such that the second time-resolved measurement data can comprise the injected contrast agent bolus. A time resolution of the second time-resolved measurement data is usually defined such that the injected contrast agent bolus can be detected using the second time-resolved measurement data. Detecting the injected contrast agent bolus can mean simply detecting a different contrast enhancement in the second time-resolved measurement data as a result of the injected contrast agent bolus. The different contrast enhancement can be defined by a threshold value. The second time-resolved measurement is preferably suitably configured for detecting a third contrast-enhancement time instant at which the contrast enhancement by the injected contrast agent bolus differs, in particular in relation to another time instant before the contrast enhancement by the injected contrast agent bolus, by more than the threshold value.

The measurement start time of the angiographic measurement can be set in particular according to the third contrast-enhancement time instant. Detecting the injected contrast agent bolus in the second measurement region can correspond to determining the third contrast-enhancement time instant. The measurement start time of the angiographic measurement can usually be set once the third contrast-enhancement time instant in the second measurement region has been detected by the second time-resolved measurement. The measurement start time of the angiographic measurement is usually set immediately after the third contrast-enhancement time instant is detected. Preferably, the measurement start time of the angiographic measurement can be set such that the angiographic measurement is performed immediately after the second time-resolved measurement. By setting the measurement start time of the angiographic measurement, a measurement end time of the second time-resolved measurement can also be set. For example, the second time-resolved measurement is stopped immediately after the detection of the injected contrast agent bolus by setting the measurement end time of the second time-resolved measurement. In addition in this case, the angiographic measurement can be started after a pause or immediately if the measurement start time of the angiographic measurement is set accordingly.

The injected contrast agent bolus can be detected preferably both in the first measurement region and in the second measurement region and also in the main measurement region. This means in particular that only a single contrast agent bolus needs to be injected in order to perform the angiographic measurement. The first time-resolved measurement, the second time-resolved measurement and the angiographic measurement and also the time at which the contrast agent bolus is injected can together define an angiographic measurement protocol. In the event of an unsuitable configuration of the angiographic measurement protocol, for instance by an incorrect time sequence or unsuitable configuration of the first time-resolved measurement, of the second time-resolved measurement, of the angiographic measurement and the time at which the contrast agent bolus is injected, it can happen that the injected contrast agent bolus cannot be detected. The first time-resolved measurement, the second time-resolved measurement and the angiographic measurement must usually be performed one after the other, with in particular the first time-resolved measurement being performed earlier in time than the second time-resolved measurement, and the second time-resolved measurement being performed earlier in time than the angiographic measurement.

If the angiographic measurement protocol comprises the second time-resolved measurement, the first time-resolved measurement can usually be stopped, and the second time-resolved measurement started, after the injected contrast agent bolus is detected in the first measurement region. In particular, the second time-resolved measurement can be stopped and the angiographic measurement can be started after the injected contrast agent bolus is detected in the second measurement region.

If the injected contrast agent bolus is detected by the second time-resolved measurement, the at least one measurement parameter can preferably be set such that the difference between the measurement start time of the angiographic measurement and the measurement end time of the angiographic measurement, and in particular the measurement duration of the angiographic measurement, are kept constant. Alternatively or additionally, it is also conceivable that by setting the measurement start time of the angiographic measurement according to the injected contrast agent bolus detected in the second measurement region, at least one time parameter and/or at least one sequence parameter, for example, is set or adjusted. If at least one sequence parameter is set, for instance, such that the measurement duration of the angiographic measurement varies, redefinition of another at least one sequence parameter may take place.

The at least one measurement parameter of the angiographic measurement is set in particular using a second transit time of the injected contrast agent bolus, wherein a second path is defined between the second measurement region and the main measurement region, and the second transit time of the injected contrast agent bolus along the second path is calculated using the flow rate of the injected contrast agent bolus determined in the first measurement region. The second transit time of the injected contrast agent bolus can equal the magnitude of the difference between a fourth contrast-enhancement time instant and a fifth contrast-enhancement time instant. For instance, the fourth contrast-enhancement time instant and the fifth contrast-enhancement time instant can be determined by detecting the injected contrast agent bolus respectively at a first end of the second path and at a second end of the second path. Alternatively or additionally, the fourth contrast-enhancement time instant and the fifth contrast-enhancement time instant can be determined by defining the second path. The second transit time can either be determined by the user of the magnetic resonance system or in particular automatically.

The second path is preferably defined by the user of the magnetic resonance system, for instance on the graphical user interface. The user can interact with the graphical user interface for this purpose. For instance, the overview-measurement data is used to help define the second path. The second path is usually located between the second measurement region and the main measurement region. The second measurement region and the main measurement region can preferably each comprise either the first end of the second path or the second end of the second path. In another embodiment, the second path is defined along the vascular structure detected by way of the overview-measurement data.

The at least one measurement parameter of the angiographic measurement can be adjusted to suit the second transit time of the injected contrast agent bolus. For example, the greater the second transit time, the later can be set the measurement start time of the angiographic measurement.

In another embodiment, the overview-measurement data is used to determine the second path between the second measurement region and a subregion of the main measurement region. The subregion of the main measurement region can usually be contained entirely in the main measurement region. The subregion is normally smaller than the main measurement region. The subregion of the main measurement region can preferably comprise a medically relevant structure or morphology, in particular arteries and/or veins of the vascular structure.

In one embodiment, setting the at least one measurement parameter of the angiographic measurement using the second transit time of the injected contrast agent bolus comprises setting on the basis of the second transit time, a center time of the angiographic measurement, which center time corresponds to acquisition of a central region of a k-space of the main measurement region. The center time equals in particular the time at which the angiographic measurement acquires the central region of k-space. The central region usually comprises a region around an origin of k-space. The central region of k-space in particular can contain the low frequency components of the angiographic measurement in comparison with the high frequency components of the angiographic measurement in a peripheral part of k-space. The central region of k-space is thus advantageously responsible for the contrast, while the peripheral part of k-space is instead responsible for the details of the angiographic measurement. The center time usually lies between the measurement start time of the angiographic measurement and the measurement end time of the angiographic measurement.

If the center time is set on the basis of the second transit time, the central region of a k-space of the main measurement region can correspond in particular to that subregion that comprises at least the first end or the second end of the second path. In particular, the subregion of the main measurement region can preferably be detected by the angiographic measurement such that the center time corresponds to a time instant of the maximum contrast enhancement by the injected contrast agent bolus.

In principle, it is conceivable that the flow rate in the first measurement region is determined, on the basis of which the at least one measurement parameter is set, and that by detecting the injected contrast agent bolus by way of the first time-resolved measurement, the measurement start time of the angiographic measurement is also set. This configuration is possible particularly in those cases in which the first measurement region is positioned so far from the main measurement region that setting the at least one measurement parameter is technically feasible in particular before the contrast-enhancement of the main measurement region by the injected contrast agent bolus, and the angiographic measurement can be started using the at least one measurement parameter that has been set. If the first measurement region is defined too far from the main measurement region, or a third path between the first measurement region and the main measurement region cannot be determined, it can be disadvantageous particularly if the angiographic measurement is started after a pause or immediately after the injected contrast agent bolus is detected in the first measurement region.

The first time-resolved measurement, the second time-resolved measurement and the angiographic measurement are advantageously performed automatically, with the associated first measurement region, second measurement region or main measurement region being positioned in the maximum field of view of the system. For example, the first time-resolved measurement, the second time-resolved measurement and the angiographic measurement can be performed more than once, preferably without adjusting the measurement parameters. Usually only the angiographic measurement is performed twice. In particular, the contrast agent bolus is injected after the angiographic measurement is performed for a first time, and before the angiographic measurement is performed for a second time. An injector, for example, can be used to perform the injection. The time instant of the injection can typically be set by the user or in an automated manner. Thus, for example, the main measurement region is measured twice by the angiographic measurement, wherein the measurement parameters of the two angiographic measurements preferably do not differ, and only the time parameters, in particular the measurement start time and the measurement end time of the two angiographic measurements, differ.

The angiogram can typically be produced from the angiographic measurements carried out. Preferably, angiographic images are determined on the basis of the angiographic measurements in order to produce in particular the angiogram using the angiographic images. The angiogram of the patient is usually produced by subtraction of the angiographic images before the injection of the contrast agent bolus and of the angiographic images after the injection of the contrast agent bolus. In this case, the angiogram corresponds essentially simply to detecting the injected contrast agent bolus within the vascular structure of the patient. The angiogram is preferably produced automatically by suitable algorithms on the basis of the angiographic images of the main measurement region. Alternatively or additionally, the user can also view the angiographic images separately on the graphical user interface or combine the angiographic images manually into the angiogram of the patient.

At least one embodiment of the invention relates not only to the method but also to a magnetic resonance system comprising a planning unit, a control unit and a measurement unit, which is designed to perform at least one embodiment of the method according to at least one embodiment of the invention. The statements made above relating to the method according to at least one embodiment of the invention can be applied analogously to the magnetic resonance system. Thus the magnetic resonance system is designed to implement a method for performing an angiographic measurement of a main measurement region of a patient.

The magnetic resonance system can comprise additional components, in particular a contrast-agent injector, that are needed and/or advantageous for performing a method according to at least one embodiment of the invention. Computer programs and further software, by which a processor of the planning unit and/or of the control unit and/or of the measurement unit automatically controls and/or performs a method sequence of a method according to at least one embodiment of the invention, can be stored on a memory unit of the planning unit and/or of the control unit and/or of the measurement unit.

Most of the components of the magnetic resonance system according to at least one embodiment of the invention can be embodied in the form of software components. In principle, however, some of these components can also be implemented in the form of software-aided hardware components, for instance FPGAs or the like, in particular when especially fast calculations are needed. Likewise, the required interfaces can be designed as software interfaces, for instance if all that is involved is a transfer of data from other software components. They can also be designed, however, as hardware-built interfaces driven by suitable software. Of course it is also conceivable that a plurality of the specified components are combined in the form of a single software component or software-aided hardware component.

The computer program product according to at least one embodiment of the invention can be loaded directly into a memory of a programmable control unit of a magnetic resonance system, and comprises program code segments in order to perform a method according to at least one embodiment of the invention when the computer program product is executed in the control unit of the magnetic resonance system.

The computer program product may be a computer program or comprise a computer program. The method according to at least one embodiment of the invention can thereby be performed quickly, reproducibly and robustly. The computer program product is configured such that it can use the control unit to perform the method steps according to at least one embodiment of the invention. Therefore, the control unit must have the necessary specification such as, for example, a suitable RAM, a suitable graphics card or a suitable logic unit, in order to be able to perform the respective method steps efficiently.

The computer program product is stored, for example, on a computer-readable medium or on a network or server, from where it can be loaded into the processor of a local processing unit, which may be connected directly to the magnetic resonance system or may form part of the magnetic resonance system. In addition, control data of the computer program product can be stored on an electronically readable data storage medium.

The control data in the electronically readable data storage medium can be embodied such that it performs a method according to at least one embodiment of the invention when the data storage medium is used in a control unit of the magnetic resonance system. Thus the computer program product can also constitute the electronically readable data storage medium. Examples of electronically readable data storage media are a DVD, a magnetic tape, a hard disk or a USB stick, on which is stored electronically readable control data, in particular software (see above). When this control data (software) is read from the data storage medium and stored in the control unit and/or in the planning unit and/or in the measurement unit of the magnetic resonance system, all the embodiments according to the invention of the above-described method can be performed. Hence at least one embodiment of the invention can also proceed from the computer-readable medium and/or from the electronically readable data storage medium.

Figure 1:
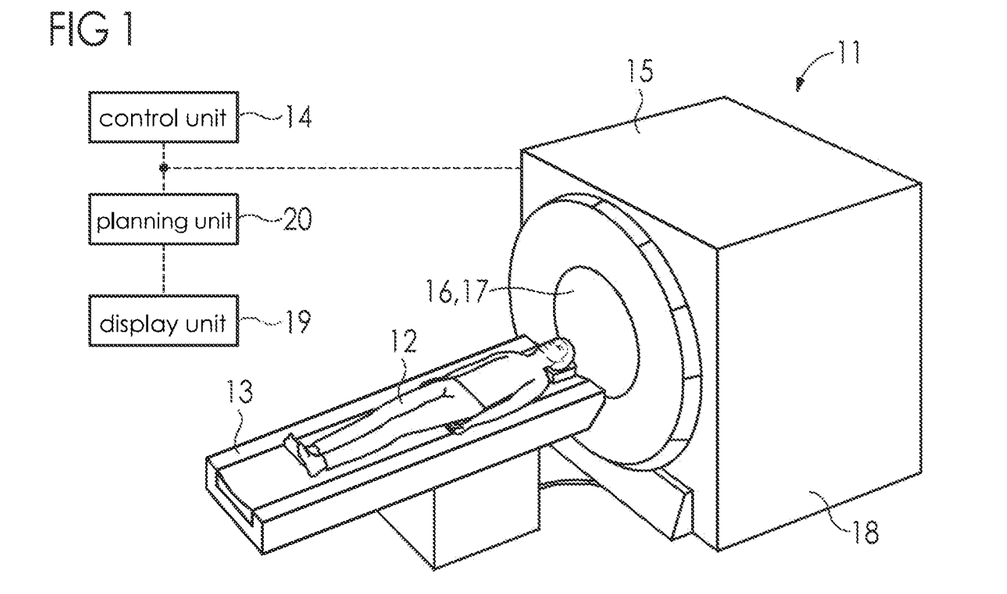
FIG. 1 shows schematically a magnetic resonance system according to an embodiment of the invention.

FIG. 1 shows schematically a magnetic resonance system 11 according to an embodiment of the invention. The magnetic resonance system 11 comprises a detector unit formed by a magnet unit 15 and containing a main magnet for generating a powerful and in particular constant main magnetic field. In addition, the magnetic resonance system 11 comprises a cylindrical patient placement zone 16 for accommodating a patient 12, the patient placement zone 16 being encircled cylindrically in a circumferential direction by the magnet unit 15.

In the present case, the patient 12 can be moved into the patient placement zone 16 of the magnetic resonance system 11 by a patient support apparatus 13 of the magnetic resonance system 11. The patient support apparatus 13 comprises for this purpose a couch, which is arranged such that it can move within the magnetic resonance system 11. The patient placement zone 16 of the magnetic resonance system 11 has a maximum field of view 17 extending in the longitudinal direction of the patient support apparatus 13 of the magnetic resonance system 11.

An enclosure casing of the magnetic resonance system 11 screens the magnet unit 15 externally. The magnet unit 13 further comprises a gradient coil unit for generating magnetic field gradients, which are used for spatial encoding during imaging. The gradient coil unit is controlled by a gradient control unit. In addition, the magnet unit comprises a radio frequency antenna unit, which in the case shown is embodied as a body coil that is permanently integrated in the magnetic resonance system 11, and a radio frequency antenna control unit for exciting a polarization which establishes itself in the main magnetic field generated by a main magnet of the magnet unit 15. The radio frequency antenna unit is controlled by the radio frequency antenna control unit and radiates high-frequency magnetic resonance sequences into an examination space, which is largely formed by the patient placement zone 16. The radio frequency antenna unit is also designed to receive magnetic resonance signals, in particular from the patient 12.

The magnetic resonance system 11 also comprises a measurement unit 18. The measurement unit 18 can be part of the magnet unit 15, for example. The measurement unit 18 can comprise the gradient coil unit and/or the radio frequency antenna unit.

The magnetic resonance system 11 comprises a control unit 14 for controlling the magnet unit 15. The control unit 14 centrally controls the magnetic resonance system 11, for instance controls the execution of a predetermined imaging gradient echo sequence.

Control data such as measurement parameters, for instance, and reconstructed magnetic resonance images can be displayed to a user on a display unit 19, for example on at least one monitor, of the magnetic resonance system 11. In addition, control data can be exchanged between the control unit 14 and a planning unit 20. The planning unit 20 typically comprises the display unit 19 and an input device, for instance a mouse or keyboard. For example, the control unit 14 can provide measurement parameters to the planning unit 20 so that the planning unit 20 displays these measurement parameters to the user on at least one monitor. In a further step, the planning unit 20 can, for example, set measurement parameters and provide these measurement parameters to the control unit 14. A user can use the planning unit 20 to enter information and/or measurement parameters during a measurement procedure.

The magnetic resonance system 11 shown can obviously include further components usually present in magnetic resonance systems 11, for instance an injector for injecting the contrast agent bolus. Likewise, the individual components, in particular the display unit 19, the control unit 14, the measurement unit 18 and the planning unit 20, can be in a different relationship to one another and/or be integrated in a higher-level unit. Furthermore, since a person skilled in the art knows how a magnetic resonance system 11 works in general, a detailed description of the further components is not given.

Figure 2:
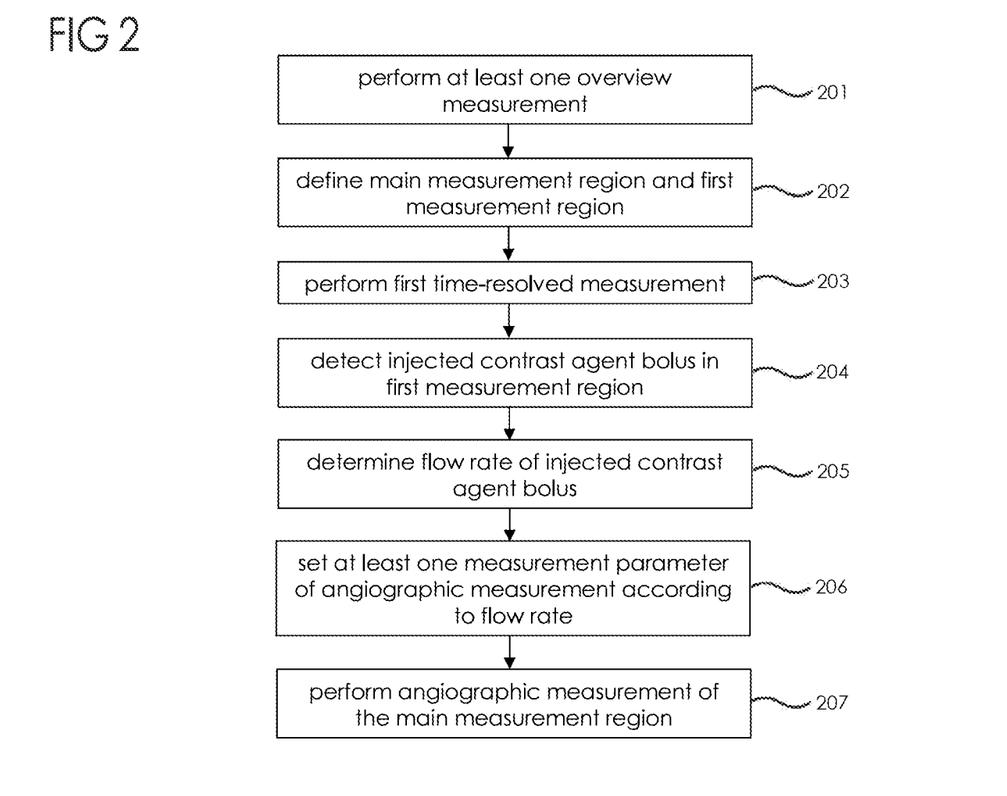
FIG. 2 shows a flow diagram of a method according to an embodiment of the invention for performing an angiographic measurement of a main measurement region of a patient via a magnetic resonance system.

FIG. 2 is a flow diagram of a method according to an embodiment of the invention for performing an angiographic measurement of a main measurement region 303 of a patient 12 via a magnetic resonance system 11. The method comprises the method steps 201-207, which method steps 201-207 are described also using description parts that include the corresponding reference signs mentioned in connection with the other figures.

Method step 201 identifies performing via the magnetic resonance system 11 at least one overview measurement, wherein overview-measurement data is generated.

Method step 202 identifies using the overview-measurement data to define the main measurement region 303 and a first measurement region 301, which differs from the main measurement region 303.

Method step 203 identifies performing via the magnetic resonance system 11 a first time-resolved measurement in the defined first measurement region 303, wherein first time-resolved measurement data is generated.

Method step 204 identifies using the first time-resolved measurement data to detect an injected contrast agent bolus in the defined first measurement region 301.

Method step 205 identifies determining a flow rate 311.F of the detected injected contrast agent bolus.

Method step 206 identifies setting at least one measurement parameter of the angiographic measurement according to the determined flow rate 311.F, and in particular setting a measurement duration of the angiographic measurement according to the determined flow rate 311.F.

Method step 207 identifies performing the angiographic measurement of the main measurement region 303 of the patient 12 in the magnetic resonance system 11 using the at least one measurement parameter that has been set.

Figure 3:
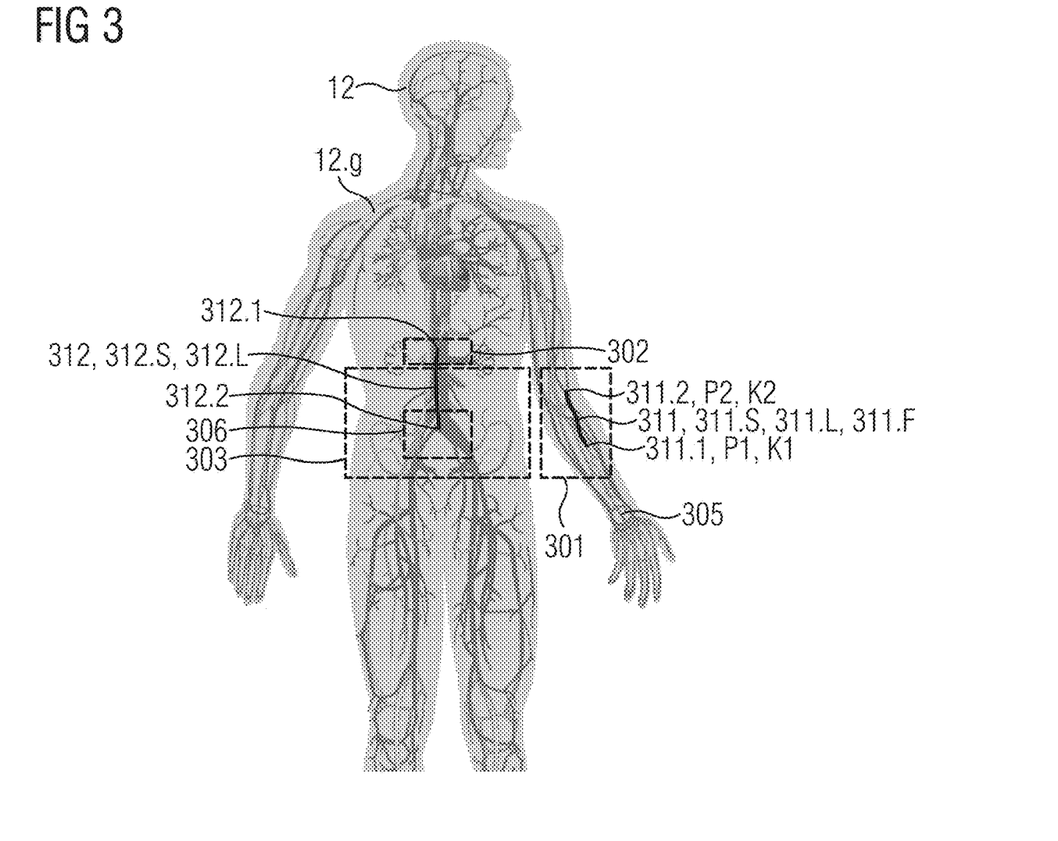
FIG. 3 illustrates defining the main measurement region 303, a first measurement region and a second measurement region using the overview-measurement data.

FIG. 3 illustrates using the overview-measurement data to define the main measurement region 303, a first measurement region 301 and a second measurement region 302. The first measurement region 301, the second measurement region 302 and the main measurement region 303 each differ from one another. The maximum field of view 17 comprises the first measurement region 301, the second measurement region 302 and the main measurement region 303. In this embodiment, the first measurement region 301 is located distal to the main measurement region 303, and the second measurement region 302 is located proximal to the main measurement region 303. The first measurement region 301 and/or the second measurement region 302 can be defined automatically according to the main measurement region 303.

The contrast agent bolus can preferably be injected at an injection position 305, where neither the first measurement region 301, nor the second measurement region 302 nor the main measurement region 303 comprise the injection position 305. The injection position 305 is preferably selected such that first the first measurement region 301, then the second measurement region 302 and finally the main measurement region 303 comprise at least some of the contrast agent bolus.

The first measurement region 301 comprises a first path 311, which has a first end 311.1 and a second end 311.2. The first end 311.1 has a first point P1, and the second end 311.2 has a second point P2. In this embodiment, the first end 311.1 corresponds to the first point P1, and the second end 311.2 corresponds to the second point P2.

The first contrast-enhancement time instant K1 is detected at the first point P1 in the first measurement region 301, and the second contrast-enhancement time instant K2 is detected at the second point P2 in the first measurement region 301. The first contrast-enhancement time instant K1 and the second contrast-enhancement time instant K2 equal the respective times at which the signal strengthened by the injected contrast agent bolus exceeds a threshold value 401 at the first point P1 and at the second point P2 respectively. The magnitude of the difference between the first contrast-enhancement time instant K1 and the second contrast-enhancement time instant K2 equals the first transit time 311.L.

In this embodiment, the first path 301 is defined along a vascular structure 12.g of the patient 12, which structure is detected using the overview-measurement data. The first path 301 has a measurable first length 311.S.

A flow rate 311.F of the injected contrast agent bolus can be calculated using the first path 311.S and the first transit time 311.L.

Setting the at least one measurement parameter of the angiographic measurement comprises in particular performing via the magnetic resonance system 11 a second time-resolved measurement in the defined second measurement region 302, wherein second time-resolved measurement data is generated, using the second time-resolved measurement data to detect the injected contrast agent bolus in the second measurement region 302, and setting a measurement start time of the angiographic measurement according to the injected contrast agent bolus detected in the second measurement region 302.

FIG. 3 shows also the subregion 306 of the main measurement region 303. The second path 312 also has a first end 312.1 and a second end 312.2, wherein the second measurement region 302 comprises the first end 312.1, and the main measurement region 303, in particular the subregion 306, comprises the second end 312.2. If, for example, the subregion 306 comprises particularly interesting information from the angiographic measurement, the second transit time 312.L can be calculated using the determined second path 312, in particular if the second end 312.2 of the second path 312 lies in the subregion 306, and the flow rate 311.F determined in the first measurement region 301.

A center time of the angiographic measurement in the main measurement region 303 is preferably set according to the second transit time 312.L such that a central region of a k-space of the main measurement region 303 is acquired when the second end 312.2 of the second path 312 comprises the injected contrast agent bolus.

Figure 4:
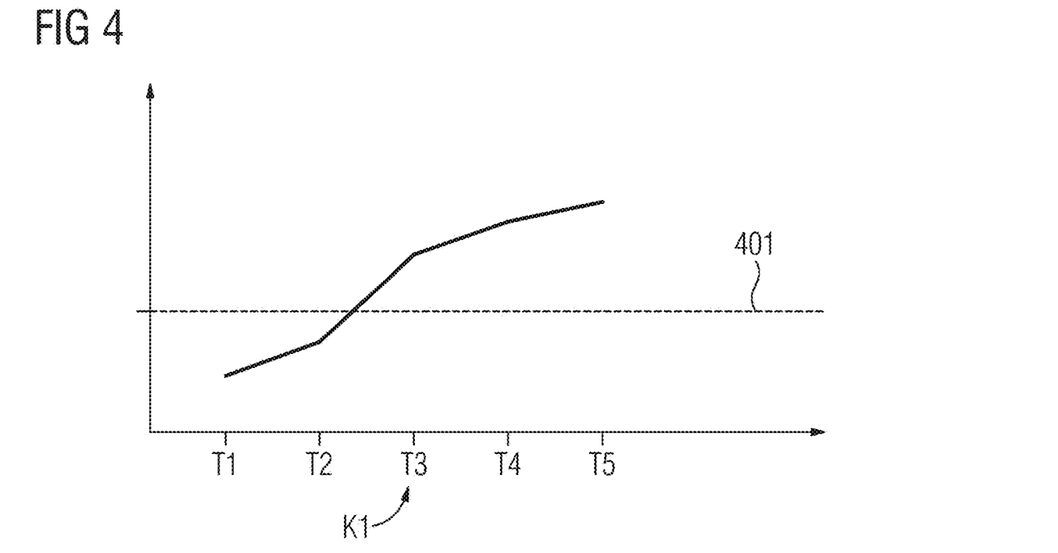
FIG. 4 shows schematically the detection of the contrast agent bolus in a contrast-enhanced vessel.

FIG. 4 shows schematically the detection of the contrast agent bolus in a contrast-enhanced vessel. The first time-resolved measurement is used to generate a series of first time-resolved measurement data at N time instants T1, T2, . . . TN−1. FIG. 4 shows an extract from the measurement data, for instance the signal in one pixel, or in a set of pixels, of the overview images over time. Detection of the injected contrast agent bolus corresponds to detecting when the signal, in particular the contrast enhancement by the injected contrast agent bolus, exceeds the threshold value 401. The first contrast-enhancement time instant K1 equals the time at which the signal exceeds the threshold value 401.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for performing an angiographic measurement of a main measurement region of a patient via a magnetic resonance system, the method comprising:
    performing, via the magnetic resonance system, at least one overview measurement to generate overview-measurement data;
    defining, using the overview-measurement data, the main measurement region and a first measurement region, the first measurement region differing from the main measurement region;
    performing, via the magnetic resonance system, a first time-resolved measurement in the first measurement region to generate first time-resolved measurement data;
    detecting an injected contrast agent bolus in the first measurement region using the first time-resolved measurement data;
    determining a flow rate of the injected contrast agent bolus;
    setting at least one measurement parameter of the angiographic measurement according to the flow rate; and
    performing the angiographic measurement of the main measurement region of the patient in the magnetic resonance system using the at least one measurement parameter set, when the same injected contrast agent bolus detected in the first measurement region is in the main measurement region,
    wherein the at least one measurement parameter includes a sequence parameter including at least one of a matrix size, a spatial resolution, a slice thickness or a repetition time of the angiographic measurement.

2. The method of claim 1, wherein the determining the flow rate comprises:
    defining a first path in the first measurement region;
    determining a first transit time, on the first path, of the injected contrast agent bolus detected in the first measurement region; and
    calculating the flow rate based on the first path and the first transit time.

3. The method of claim 2, wherein the defining the first path comprises:
    detecting a vascular structure of the patient using the overview-measurement data; and
    defining the first path along the vascular structure of the patient.

4. The method of claim 3, wherein the setting the at least one measurement parameter further comprises:
    setting a measurement duration of the angiographic measurement according to the flow rate.

5. The method of claim 2, wherein the setting the at least one measurement parameter further comprises:
    setting a measurement duration of the angiographic measurement according to the flow rate.

6. The method of claim 1, wherein the setting the at least one measurement parameter further comprises:
    setting a measurement duration of the angiographic measurement according to the flow rate.

7. The method of claim 1, further comprising:
    defining a second measurement region based on the overview-measurement data, the second measurement region differing from the first measurement region and the second measurement region differing from the main measurement region.

8. The method of claim 7, wherein the first measurement region is located distal to the main measurement region, and wherein the second measurement region is located proximal to the main measurement region.

9. The method of claim 8, wherein at least one of the first measurement region or the second measurement region is defined automatically according to the main measurement region.

10. The method of claim 8, wherein a maximum field of view of the magnetic resonance system comprises the first measurement region, the second measurement region and the main measurement region.

11. The method of claim 8, wherein the setting the at least one measurement parameter further comprises:
    performing, via the magnetic resonance system, a second time-resolved measurement in the second measurement region, to generate second time-resolved measurement data;
    detecting, using the second time-resolved measurement data, the injected contrast agent bolus in the second measurement region; and
    setting a measurement start time of the angiographic measurement according to the injected contrast agent bolus detected in the second measurement region.

12. The method of claim 7, wherein at least one of the first measurement region or the second measurement region is defined automatically according to the main measurement region.

13. The method of claim 7, wherein a maximum field of view of the magnetic resonance system comprises the first measurement region, the second measurement region and the main measurement region.

14. The method of claim 7, wherein the setting the at least one measurement parameter further comprises:
performing, via the magnetic resonance system, a second time-resolved measurement in the second measurement region, to generate second time-resolved measurement data;
detecting, using the second time-resolved measurement data, the injected contrast agent bolus in the second measurement region; and
setting a measurement start time of the angiographic measurement according to the injected contrast agent bolus detected in the second measurement region.

15. The method of claim 7, wherein
the setting the at least one measurement parameter further includes setting the at least one measurement parameter using a second transit time of the injected contrast agent bolus, and
the method further comprises:
defining a second path between the second measurement region and the main measurement region; and
calculating the second transit time of the injected contrast agent bolus along the second path using the flow rate of the injected contrast agent bolus determined in the first measurement region.

16. The method of claim 15, wherein the defining the second path further comprises:
defining the second path between the second measurement region and a subregion of the main measurement region using the overview-measurement data.

17. The method of claim 16, wherein the setting the at least one measurement parameter further comprises:
setting, based upon the second transit time, a center time of the angiographic measurement, the center time corresponding to acquisition of a central region of a k-space of the main measurement region.

18. The method of claim 16, further comprising:
detecting a vascular structure of the patient using the overview-measurement data, wherein
the defining the second path includes defining the second path along the vascular structure of the patient.

19. The method of claim 15, wherein the setting the at least one measurement parameter further comprises:
setting, based upon the second transit time, a center time of the angiographic measurement, the center time corresponding to acquisition of a central region of a k-space of the main measurement region.

20. The method of claim 15, further comprising:
detecting a vascular structure of the patient using the overview-measurement data, wherein
the defining the second path further includes
defining the second path along the vascular structure of the patient.

21. A non-transitory computer program product, directly loadable into a memory of a programmable control unit of a magnetic resonance system, including program code segments to perform the method of claim 1 when the computer program product is executed in the programmable control unit of the magnetic resonance system.

22. A non-transitory computer readable medium including program code segments for carrying out the method of claim 1 when executed on a computer.

23. The method of claim 1, wherein only one injected contrast agent bolus is used for the detecting the injected contrast agent bolus, the determining the flow rate, the setting the at least one measurement parameter, and the performing the angiographic measurement.

24. The method of claim 1, wherein
the first measurement region corresponds with at least a portion of an arm of the patient, and
the main measurement region corresponds with at least a portion of an abdomen of the patient.

25. A magnetic resonance system, comprising:
processing circuitry configured to cause the magnetic resonance system to
perform at least one overview measurement to generate overview-measurement data,
define, using the overview-measurement data, a main measurement region and a first measurement region, the first measurement region differing from the main measurement region,
perform a first time-resolved measurement in the first measurement region to generate first time-resolved measurement data,
detect an injected contrast agent bolus in the first measurement region using the first time-resolved measurement data,
determine a flow rate of the injected contrast agent bolus,
set at least one measurement parameter of an angiographic measurement according to the flow rate, and
perform the angiographic measurement of the main measurement region of a patient in the magnetic resonance system using the at least one measurement parameter set, when the same injected contrast agent bolus detected in the first measurement region is in the main measurement region,
wherein the at least one measurement parameter includes a sequence parameter including at least one of a matrix size, a spatial resolution, a slice thickness or a repetition time of the angiographic measurement.

26. A magnetic resonance system, comprising:
a memory storing computer-readable instructions; and
one or more processors configured to execute the computer-readable instructions such that the one or more processors are configured to cause the magnetic resonance system to,
perform at least one overview measurement to generate overview-measurement data;
define, using the overview-measurement data, a main measurement region and a first measurement region, the first measurement region differing from the main measurement region;
perform a first time-resolved measurement in the first measurement region to generate first time-resolved measurement data;
detect an injected contrast agent bolus in the first measurement region using the first time-resolved measurement data;
determine a flow rate of the injected contrast agent bolus;
set at least one measurement parameter of an angiographic measurement according to the flow rate; and
perform the angiographic measurement of the main measurement region of a patient in the magnetic resonance system using the at least one measurement parameter set, when the same injected contrast agent bolus detected in the first measurement region is in the main measurement region,
wherein the at least one measurement parameter includes a sequence parameter including at least one of a matrix size, a spatial resolution, a slice thickness or a repetition time of the angiographic measurement.

\* \* \* \* \*